(12) United States Patent
Smith et al.

(10) Patent No.: US 10,249,741 B2
(45) Date of Patent: Apr. 2, 2019

(54) SYSTEM AND METHOD FOR ION-SELECTIVE, FIELD EFFECT TRANSISTOR ON FLEXIBLE SUBSTRATE

(71) Applicants: Joseph T. Smith, Tempe, AZ (US); Michael Goryll, Mesa, AZ (US); Sahil Shah, Ahmendabad (IN); Jennifer Blain Christen, Chandler, AZ (US); John Stowell, Tempe, AZ (US)

(72) Inventors: Joseph T. Smith, Tempe, AZ (US); Michael Goryll, Mesa, AZ (US); Sahil Shah, Ahmendabad (IN); Jennifer Blain Christen, Chandler, AZ (US); John Stowell, Tempe, AZ (US)

( * ) Notice: Subject to any disclaimer, the term of this patent is extended or adjusted under 35 U.S.C. 154(b) by 83 days.

(21) Appl. No.: 14/710,830

(22) Filed: May 13, 2015

(65) Prior Publication Data

US 2015/0330941 A1    Nov. 19, 2015

Related U.S. Application Data

(60) Provisional application No. 61/992,374, filed on May 13, 2014.

(51) Int. Cl.
*G01N 27/414* (2006.01)
*H01L 29/66* (2006.01)
*H01L 29/786* (2006.01)

(52) U.S. Cl.
CPC ..... *H01L 29/66969* (2013.01); *G01N 27/414* (2013.01); *G01N 27/4148* (2013.01); *H01L 29/66742* (2013.01); *H01L 29/786* (2013.01)

(58) Field of Classification Search
CPC .................................................. G01N 27/414
See application file for complete search history.

(56) References Cited

U.S. PATENT DOCUMENTS

| | | |
|---|---|---|
| 4,180,771 A | 12/1979 | Guckel |
| 7,598,546 B1 | 10/2009 | Chou et al. |
| 7,649,358 B2 | 1/2010 | Toumazou et al. |
| 8,097,926 B2 | 1/2012 | De Graff et al. |
| 8,367,461 B2 | 2/2013 | Kuegler et al. |
| 8,481,859 B2 | 7/2013 | Haq et al. |
| 8,685,201 B2 | 4/2014 | O'Rourke et al. |
| 8,992,712 B2 | 3/2015 | Loy et al. |
| 8,999,778 B2 | 4/2015 | O'Rourke et al. |
| 9,076,822 B2 | 7/2015 | Loy et al. |
| 9,155,190 B2 | 10/2015 | Haq et al. |
| 2004/0035699 A1 | 2/2004 | Hsiung et al. |

(Continued)

OTHER PUBLICATIONS

Smith et al., "Flexible ISFET Biosensor Using IGZO Metal Oxide TFTs and an ITO Sensing Layer", IEEE Sensors Journal, vol. 14, No. 4, pp. 937-938, Apr. 2014.

(Continued)

*Primary Examiner* — Mounir S Amer
(74) *Attorney, Agent, or Firm* — Quarles & Brady LLP

(57) ABSTRACT

A flexible ion-selective field effect transistor (ISFET) and methods of making the same are disclosed. The methods may comprise: (a) attaching a flexible substrate to a rigid support with an adhesive; (b) forming an ion-selective field effect transistor structure on a surface of the flexible substrate; and (c) removing the flexible substrate from the rigid support after step (b).

12 Claims, 10 Drawing Sheets

(56) References Cited

U.S. PATENT DOCUMENTS

| | | | |
|---|---|---|---|
| 2005/0181566 A1* | 8/2005 | Machida | H01L 29/66757 438/301 |
| 2005/0230271 A1* | 10/2005 | Levon | G01N 27/4148 205/789 |
| 2006/0035400 A1 | 2/2006 | Wu et al. | |
| 2008/0136989 A1* | 6/2008 | Higaki | H01L 27/12 349/46 |
| 2009/0321792 A1 | 12/2009 | Chou et al. | |
| 2010/0140089 A1 | 6/2010 | Chou et al. | |
| 2011/0018038 A1 | 1/2011 | Yeh et al. | |
| 2011/0169056 A1 | 7/2011 | Wey et al. | |
| 2011/0283821 A1 | 11/2011 | Ober et al. | |
| 2013/0105868 A1* | 5/2013 | Kalnitsky | G01N 27/414 257/288 |
| 2013/0200438 A1* | 8/2013 | Liu | G01N 27/414 257/253 |
| 2014/0008651 A1 | 1/2014 | Marrs | |
| 2014/0170661 A1* | 6/2014 | Lamura | C12Q 1/6825 435/6.11 |
| 2014/0183520 A1* | 7/2014 | Chang | H01L 29/66969 257/43 |
| 2015/0129937 A1* | 5/2015 | Chen | G01N 27/4145 257/253 |
| 2015/0184237 A1* | 7/2015 | Su | C12Q 1/6874 435/6.1 |

OTHER PUBLICATIONS

Bergveld, "Thirty years of ISFETOLOGY—What happened in the past 30 years and what may happen in the next 30 years," Sens. Actuators B, vol. 88, No. 1, pp. 1-20, 2003.
Meyberg et al., "N-channel field-effect transistors with floating gates for extracellular recordings," Biosensors Bioelectron., vol. 21, No. 7, pp. 1037-1044, 2006.
Estrela et al., "Application of thin film transistors to label-free electrical biosensors," Proc. IEEE Int. Symp. Ind. Electron., Jun./Jul. 2008, pp. 2034-2039.
Pinto et al., "Extended-gate ISFETs based on sputtered amorphous oxides," Journal of Display Technology, vol. 9, No. 9, pp. 729-734, Sep. 2013.
O'Brien et al., "70.2L: Late-News Paper: 14.7" active matrix PHOLED displays on temporary bonded PEN substrates with low temperature IGZO TFTs," SID Symp. Dig. Tech. Papers, pp. 447-450, 2013.
Bergveld, Development of an ion-sensitive solid-state device for neurophysiological measurements, IEEE Transactions on Biomedical Engineering, pp. 70-71, 1970.
Jimenez-Jorquera, et al., "ISFET based microsensors for environmental monitoring", Sensors 10 pp. 61-83, 2010.
Sharon et al., "Detection of explosives using field-effect transistors", Electroanalysis 21 pp. 2185-2189, 2009.
Lee et al., "Ion-sensitive field-effect transistor for biological sensing", Sensors 9 pp. 7111-7131, 2009.
Kim et al., "An FET-type charge sensor for highly sensitive detection of DNA sequence", Biosensors and Bioelectronics 20 pp. 69-74, 2004.
Toumazou et al., "Simultaneous DNA amplification and detection using a pH-sensing semiconductor system", Nature Methods, vol. 10 No. 7, pp. 641-648, 2013.
Rothberg et al., "An integrated semiconductor device enabling non-optical genome sequencing", Nature 475 pp. 348-352, 2011.
Selvanayagam et al., , "An ISFET-based immunosensor for the detection of beta-bungarotoxin", Biosensors and Bioelectronics ,17 pp. 821-826, 2002.
Schoning et al., "Recent advances in biologically sensitive field-effect transistors (BioFETs)", Analyst 127, pp. 1137-1151, 2002.
Welch et al., "Experimental and simulated cycling of ISFET electric fields for drift reset", IEEE Electron Device Letters 34 (3) pp. 456-458, 2013.

Van Den Vlekkert et al., "Multi-ion sensing device for horticultural application based upon chemical modification and special packaging of ISFETs", Sensors and Actuators B pp. 34-37, 1992.
Khan et al., "Microfluidics: A focus on improved cancer targeted drug delivery systems", Journal of Controlled Release 172 pp. 1065-1074, 2013.
Majedi et al., "Microfluidic assisted self-assembly of chitosan based nanoparticles as drug delivery agents", Lab Chip 13 pp. 204-207, 2013.
Weibel et al., "Microfabrication meets microbiology", Nature Reviews—Microbiology 5 pp. 209-218, 2007.
Christen et al., "Integrated PDMS/CMOS Microsystem for Autonomous Incubation and Imaging in Cell Culture Studies", Life Science Systems and Applications Workshop, IEEE/NLM, pp. 1-2, 2006.
Christen et al., "Design, Fabrication, and Testing of a Hybrid CMOS/PDMS Microsystem for Cell Culture and Incubation", IEEE Transactions on Biomedical Circuits and Systems, vol. 1, No. 1, pp. 3-18, 2007.
Welch et al., "Real-time feedback control of pH within microfluidics using integrated sensing and actuation", Lab Chip 14 pp. 1191-1197, 2014.
Son et al., "Multifunctional wearable devices for diagnosis and therapy of movement disorders", Nature Nanotechnology, vol. 9, pp. 397-404, 2014.
Rogers et al., "A curvy, stretchy future for electronics", Proceedings of the National Academy of Sciences 106, pp. 10875-10876, 2009.
Georgiou et al., "ISFET characteristics in CMOS and their application to weak inversion operation", Sensors and Actuators B: Chemical 143 pp. 211-217, 2009.
Raupp et al., "Low-temperature amorphous-silicon backplane technology development for flexible displays in a manufacturing pilot-line environment", Journal of the Society for Information Display 15 pp. 445-454, 2007.
Haq et al., "Temporary bond-debond technology for high-performance transistors on flexible substrates", Journal of the Society for Information Display 18, pp. 884-891, 2010.
Marrs et al., Control of Threshold Voltage and Saturation Mobility Using Dual-Active-Layer Device Based on Amorphous Mixed Metal—Oxide—Semiconductor on Flexible Plastic Substrates, IEEE Transactions on Electron Devices, vol. 58, No. 10., pp. 3428-3434, 2011.
Chiang et al., Hydrogen ion sensors based on indium tin oxide thin film using radio frequency sputtering system, Thin Solid Films 517 pp. 4805-4809, 2009.
Ito et al., "ISFET's with Ion-Sensitive Membranes Fabricated by Ion Implantation", IEEE Transactions on Electron Devices, vol. ED-35, No. 1, pp. 56-64, 1988.
Pelgrom et al., ",Matching properties of MOS transistors", IEEE Journal of Solid-State Circuits, 24 pp. 1433-1439, 1989.
Welch et al., "Seamless integration of CMOS and microfluidics using flip chip bonding", Journal of Micromechanics and Microengineering 23, 035009, (7 pp) 2013.
Gotoh et al., "Construction of Amorphous Silicon ISFET", Sensors and Actuators, 16 pp. 55-65, 1989.
Huang et al., "Development of an IrOx Micro pH Sensor Array on Flexible Polymer Substrate", Proc. of SPIE vol. 6931, 693104 (9 pp) 2008.
Ji et al., "In vitro evaluation of flexible pH and potassium ion-sensitive organic field effect transistor sensors", Appl. Phys. Lett. 92, 233304 (3 pp) 2008.
Kolodziej et al., "Optimization of properties of ion sensitive amorphous silicon (a-Si:H) based transistor", Proc. of SPIE vol. 3054, pp. 181-186, 1997.
Loi et al., "Flexible, organic, ion-sensitive field-effect transistor", Applied Physics Letters 86, 103512 (3 pp) 2005.
Kumar et al., "Nanowire-organic thin film transistor integration and scale up towards developing sensor array for biomedical sensing applications", Proc. of SPIE vol. 7646, 76461M (8 pp) 2010.
Reyes et al., "ZnO thin film transistor immunosensor with high sensitivity and selectivity", Applied Physics Letters 98, 173702 (3 pp) 2011.

(56) References Cited

OTHER PUBLICATIONS

Yang et al., "Nano-IGZO layer for EGFET in pH sensing characteristics", 2013 IEEE 5th International Nanoelectronics Conference, pp. 480-482, 2013.
Spijkman et al., "Dual-Gate Thin-Film Transistors, Integrated Circuits and Sensors", Adv. Mater., 23, pp. 3231-3242, 2011.
Metzker, "Sequencing technologies—the next generation", Nature Reviews | Genetics vol. 11, pp. 31-46, 2010.
Dzyadevych et al., "Enzyme biosensors based on ion-selective field-effect transistors", Analytica Chimica Acta 568, pp. 248-258, 2006.
Haq et al., "Temporary bond-debond process for manufacture of flexible electronics: Impact of adhesive and carrier properties on performance", Journal of Applied Physics 108, 114917 97 pp) 2010.

* cited by examiner

SYSTEM AND METHOD FOR ION-SELECTIVE, FIELD EFFECT TRANSISTOR ON FLEXIBLE SUBSTRATE

CROSS-REFERENCE TO RELATED APPLICATIONS

This application claims priority to U.S. Provisional Patent Application No. 61/992,374, filed May 13, 2014, the entire contents of which are incorporated herein in their entirety by reference.

STATEMENT REGARDING FEDERALLY SPONSORED RESEARCH

This invention was made with government support under W911NF-04-2-005 awarded by the Army Research Office. The government has certain rights in the invention.

BACKGROUND

This disclosure relates generally to ion-selective field effect transistors (ISFETs) on flexible substrates.

Throughout this disclosure, reference documents are identified by bracketed numbers. The reference corresponding to each bracketed number is identified herein. Each of these references is incorporated herein in its entirety by reference.

The ion-sensitive field effect transistor (ISFET) is well established as a pH sensitive biosensor, [5] and biochemical sensing is possible if a biological recognition material is immobilized on the ISFET gate-sensor surface. These devices are typically configured as large parallel arrays of individually addressed extended-gate ISFETs, and manufactured on silicon CMOS wafers. [12] While large-area ISFETs are desirable because of their large sensitive capture area, manufacturing them using a CMOS wafer fabrication process can become cost prohibitive. Commercial high volume thin film transistor (TFT) technology, used to manufacture large-area organic light emitting diode (OLED) and liquid crystal displays (LCD), offers a lower cost alternative to also produce large-area ISFET biosensors. [15] However, prior TFT-based biosensor development was limited to producing and characterizing ISFETs on rigid, fragile glass substrates. [15] [16] This can restrict the range of diagnostic applications in which the biosensor must come in direct contact with human tissue, or in direct contact with food or drink, where the ISFET biosensor may need to be conformable and/or shatterproof.

An Ion-Sensitive Field Effect Transistor (ISFET) is a pH sensor first introduced in 1970 by Bergveld [1]. Their use as a pH sensor has been extensive because of their small size, robust and low power consumption. ISFETs have seen their use as pH sensor for variety of applications such as environment monitoring [2], explosive detection [3] and for developing low cost medical devices [4][5]. Due to limitation of optical methods to detect DNA [6] [7] there has been a shift towards non-optical FET based sequencing [8] [9]. Additionally, antibodies could be immobilized on the ISFET for pathogen detection [10] [11].

In practice, these devices are typically configured as large parallel arrays of individually addressed ISFETs, and manufactured on silicon CMOS wafers [12]. However, the sensing array size for conventional ISFETs on silicon wafer substrates is ultimately constrained by a photolithographic stepper field size limited to approximately 1 cm$^2$ per die. Also the commercial use of the ISFETs has been limited due to the drift in the threshold voltage, which could be mitigated using vertical field cycling [13], and the difficulties in packaging the ISFET on a silicon wafer [14]. One solution to these conventional silicon CMOS ISFET limitations is to apply thin film transistor (TFT) technology, presently in wide use to manufacture large liquid crystal displays, to produce ISFET-based biosensors [15]. This enables sensing arrays to be much larger in area than silicon substrate ISFETs. Leveraging the scaling advantages of traditional liquid crystal display (LCD) TFT display technology, which can now manufacture displays on Gen11 sized substrates that approach 10 m$^2$, also offers the additional advantage of dramatically reducing the sensor cost to pennies per cm$^2$, which is key for disposable applications. However, prior TFT-based biosensor development was limited to fabricating and characterizing ISFETs on rigid and fragile glass substrates [16]. This can create a problem in food industry or water-quality monitoring applications, where the use of materials that can shatter is strictly forbidden [17].

Consequently, considering such limitations of previous technological approaches, it would be desirable to have a system and method for making a flexible ISFET.

SUMMARY

The present disclosure overcomes the aforementioned drawbacks by presenting apparatuses and methods for making a flexible ISFET.

In accordance with the present disclosure, systems and methods may comprise: (a) attaching a flexible substrate to a rigid support with an adhesive; (b) forming an ion-selective field effect transistor structure on a surface of the flexible substrate; and (c) removing the flexible substrate from the rigid support after step (b).

In accordance with the present disclosure, a flexible ion-selective field effect transistor can include a flexible substrate, a thin film transistor disposed on the flexible substrate, the thin film transistor including a source, a drain, a gate, and an active channel layer that are isolated from the atmosphere, and a surface sensing layer in electronic communication with the gate.

In accordance with the present disclosure, a flexible pH sensor can include a flexible substrate, a thin-film transistor disposed on the flexible substrate, and a surface sensing layer comprising a material suitable for use as a transparent top electrode in a flexible organic light emitting diode.

The foregoing and other aspects and advantages of the disclosure will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

DETAILED DESCRIPTION

Before the present disclosure is described in further detail, it is to be understood that the disclosure is not limited to the particular embodiments described. It is also to be understood that the terminology used herein is for the purpose of describing particular embodiments only, and is not intended to be limiting. The scope of the present disclosure will be limited only by the claims.

As used herein, the singular forms "a", "an", and "the" include plural embodiments unless the context clearly dictates otherwise.

Specific structures, devices, transistors, and methods relating to flexible optical biosensors have been disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Aspects referenced as "comprising" certain elements are also contemplated as "consisting essentially of" and "consisting of" those elements. It should be appreciated that terms such as source, drain, and gate are interchangeable with respective terms source electrode, drain electrode, and gate electrode.

Figure 1:
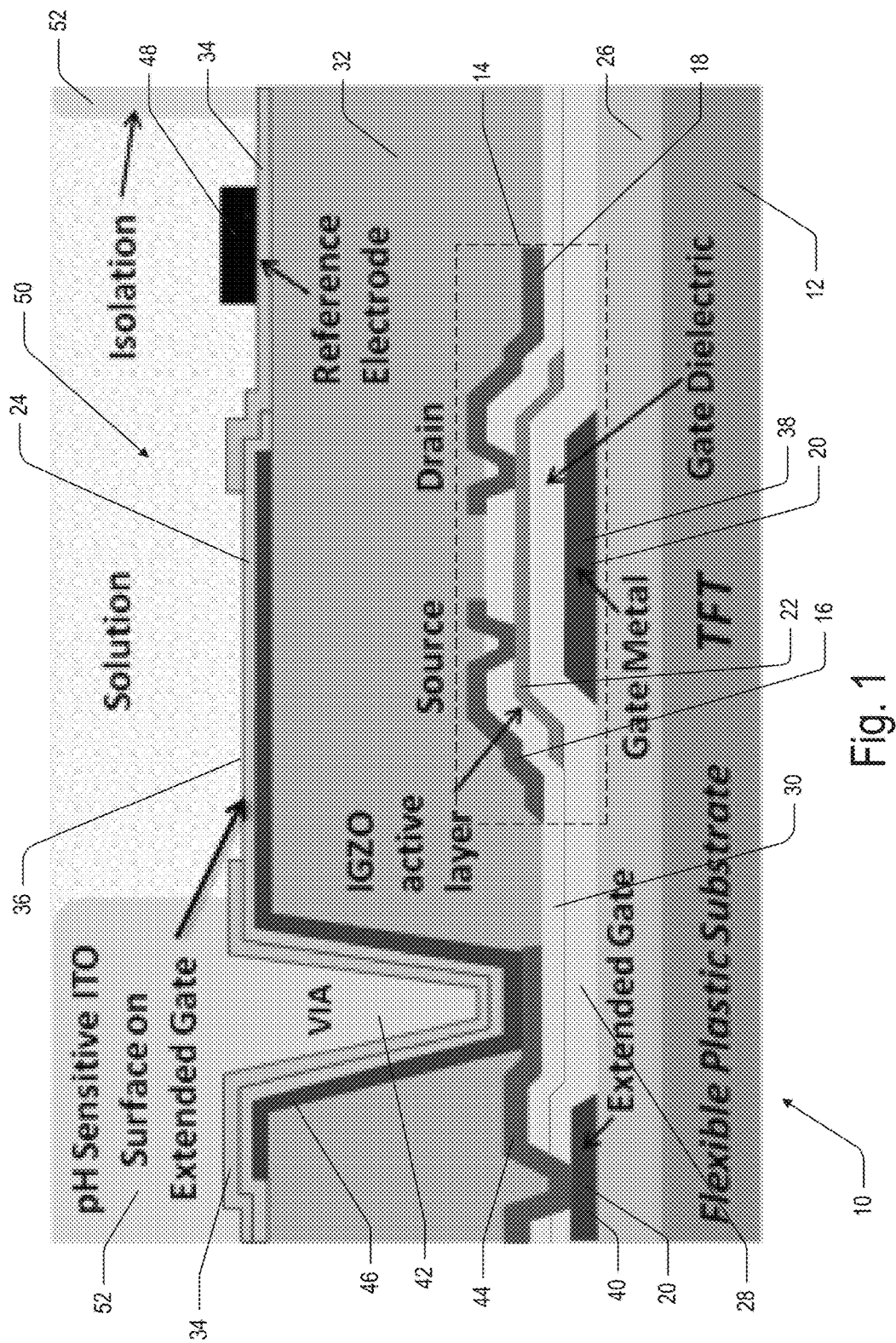
FIG. 1 a cross-section of one aspect of the flexible extended gate ISFET pH biosensor of the present disclosure, with a W/L=200 μm/9 μm bottom-gate mixed oxide (IGZO) n-channel TFT and a 1 mm×1 mm extended gate ITO pH sensor layer.

This disclosure provides a device that functions as a flexible ion-selective field effect transistor. Referring to FIG. 1, the device 10 can include a flexible substrate 12; a thin-film transistor 14 including a source 16, a drain 18, a gate 20, and an active channel layer 22; and a surface sensing layer 24 in electronic communication with the gate 20. The source 16, the drain 18, the gate 20, the active channel layer 22, or the thin-film transistor 14 can be isolated from the atmosphere. The device 10 can further include the following: a first barrier layer 26 deposited atop the flexible substrate, which can serve as an etch stop, a moisture barrier, or both; a gate dielectric layer 28, which can provide electronic isolation between the gate 20 and the active channel layer 22; a first passivation layer 30, which covers the active channel layer prior to the formation of openings; an inter-level dielectric layer 32 covering the source 16 and drain 18; and a surface passivation layer 34, covering the entire structure, with the exception of a sensing portion 36 of the surface sensing layer 24 (i.e., the exposed top surface of the surface sensing layer 24). It should be appreciated that the gate dielectric layer 28 and the first passivation layer 30 can be formed of the same material, and can form a single layer in certain locations of the device 10.

The gate 20 can include an active portion 38, which interacts with the active channel layer 22, and an extended gate portion 40, which is remote from the thin-film transistor 14 and allows a via 42 to be created without disturbing the structure of the thin-film transistor 14. The via 42 provides a route to establish electronic communication between the surface sensing layer 24 and the gate 20. In some aspects, as illustrated in FIG. 1, the extended gate portion 40 is contacted by a first extended gate metal contact 44 that is formed within an opening in the first passivation layer 30 and the inter-level dielectric layer 32. A second extended gate metal contact 46 can be deposited in the via 42 and contacting the first extended gate metal contact 44. One particular arrangement of layers and contacts is shown for providing electronic communication between the second extended gate metal contact 46 and the gate 20, but it should be appreciated that electronic communication can be formed in other ways. For example, the via 42 can be formed to provide direct access to the extended gate portion 40, and the second extended gate metal contact 46 can directly contact the extended gate portion 40.

In certain aspects, the device 10 can include a reference electrode 48, which can be used to establish a baseline reference measurement by the methods described herein or by other methods known to those having ordinary skill in the art.

In certain aspects, the device 10 can include a sample well 50. The sample well 50 can be formed by applying an isolation barrier 52 to the top of the surface passivation layer 44, leaving the below the sample well uncovered, and applying the isolation barrier to a height that equals the preferred depth for the sample well.

The various layers and other features of the device 10 described herein can be composed of the materials described in the method steps which follow or those described in U.S. Pat. Nos. 8,481,859 and 8,685,519 and U.S. Patent Application Pub. Nos. 2010/0297829, 2013/0075739, and 2014/0065389, each of which is incorporated herein in its entirety by reference.

In certain aspects, this disclosure also provides a sensor array comprising a plurality of the flexible ISFETs described herein. In certain aspects, two or more of the plurality of the flexible ISFETs can be sensitive to different analytes, for example, by having different surface sensing layers.

In certain aspects, this disclosure provides a microfluidic device comprising a microfluidic channel in fluid communication with a microfluidic reservoir, and a flexible ISFET as described herein, wherein a fluid in the microfluidic reservoir contacts at least part of the surface sensing layer, and optionally contacts at least part of a reference electrode.

In certain aspects, this disclosure provides a flexible pH sensor comprising a flexible substrate, a thin-film transistor disposed on the flexible substrate, and a surface sensing layer comprising a material suitable for use as a transparent top electrode in a flexible OLED, such as ITO.

This disclosure provides methods of making a device. In certain aspects, the methods may comprise one or more of the following steps: attaching a flexible substrate to a rigid support with an adhesive; forming an ion-selective field effect transistor structure on a surface of the flexible substrate; and removing the flexible substrate from the rigid support. The methods may further comprise forming a reference electrode. Forming an ion-selective field effect transistor structure on the surface of the flexible substrate can comprise forming a thin film transistor on the surface of the flexible substrate, the TFT having a source, a drain, and a gate, the gate isolated from the atmosphere, and forming a surface sensing layer that is exposed to the atmosphere and in electronic communication with the gate.

In certain aspects, attaching a flexible substrate to a rigid support with an adhesive and removing the flexible substrate from the rigid support can include the methods described in U.S. Pat. Nos. 8,481,859 and 8,685,519 and U.S. Patent Application Pub. Nos. 2010/0297829, 2013/0075739, and 2014/0065389, each of which is incorporated herein in its entirety by reference. In addition, other processes for attaching a flexible substrate to a rigid support with an adhesive and removing the flexible substrate from the rigid support may be suitable for use with the present disclosure.

In certain aspects, forming an ISFET structure may comprise one or more methods steps disclosed in U.S. Patent Application Pub. Nos. 2012/0061672 and 2014/0008651, each of which is incorporated herein in its entirety by reference. In addition, other method steps for forming an ISFET may be suitable for use with the present disclosure.

The ISFET structure may comprise a mixed oxide thin film transistor or an amorphous silicon thin film transistor. The ISFET structure may comprise a device structure that is bottom gate, inverted, staggered, or a combination thereof. In some aspects, the ISFET structure may comprise an etch stop TFT configuration or a back channel etched TFT configuration. It should be appreciated that this disclosure describes one arrangement in significant detail, but the concepts described herein are applicable to other TFT configurations.

The method may be performed at a temperature that is lower than a deformation temperature of the substrate. For example, when the flexible substrate has a deformation temperature of about 200° C., the method may be performed at a temperature of at most about 200° C. It should be appreciated that as new materials having higher deformation temperatures are developed that are suitable as flexible substrates, the methods described herein can be performed at higher temperatures.

In certain aspects, forming an ISFET may comprise one or more of the following: forming a gate electrode layer; forming an oxide gate dielectric layer; forming an active channel layer; forming a protective passivation layer; opening contacts to the active channel layer; forming a source/drain metal layer; forming an inter-level dielectric layer; opening vias to the source/drain metal layer; forming a first metal extended gate layer; and forming an extended gate sensing layer.

Figure 12:
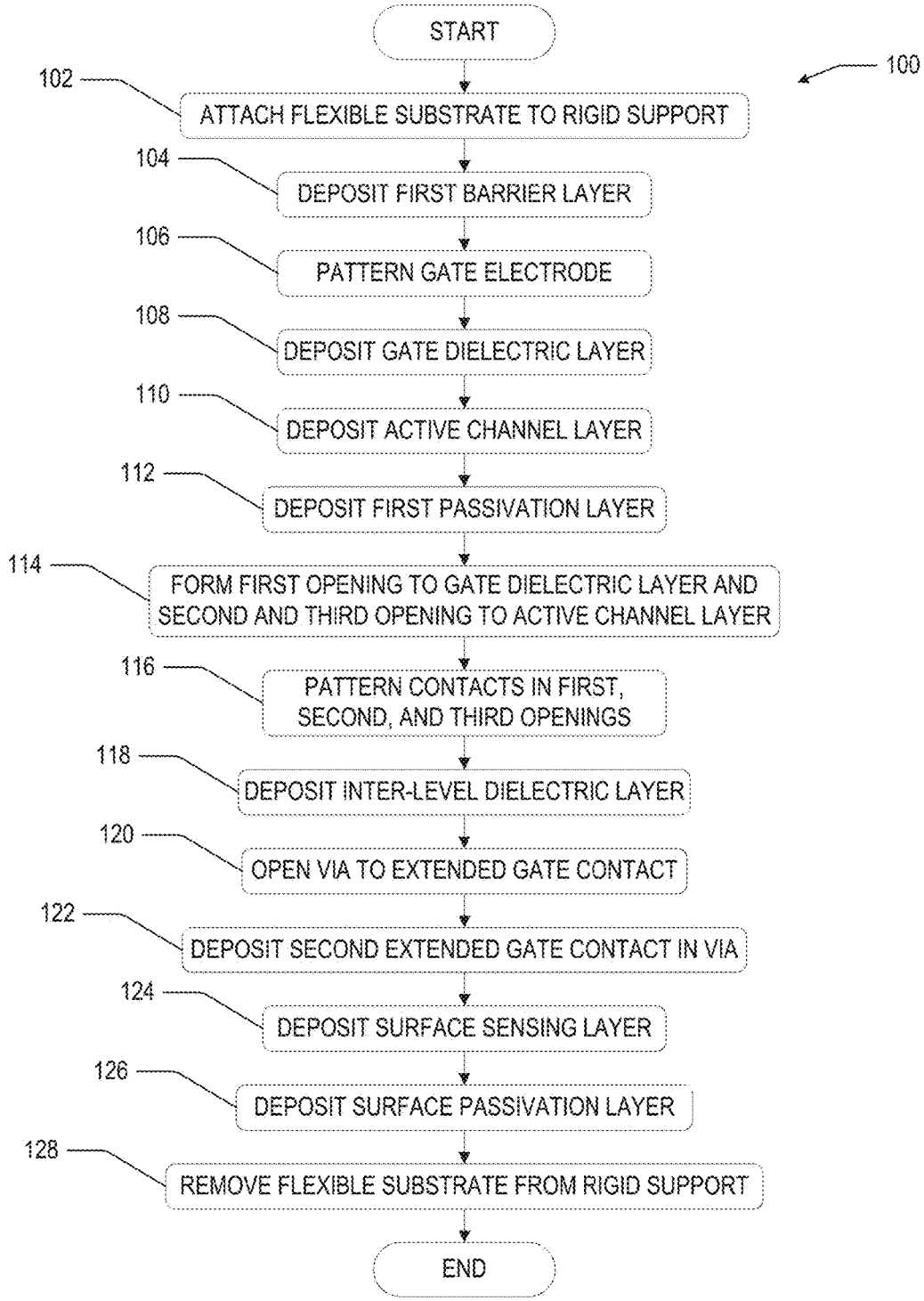
FIG. 12 is a flowchart showing a method according to one aspect of the present disclosure.

In certain aspects, referring to FIG. 12, a flowchart of a method 100 of forming a flexible ISFET is shown. At process block 102, the method 100 can include attaching a flexible substrate to a rigid support with an adhesive. At process block 104, the method 100 can include depositing a first barrier layer on the flexible substrate on a surface opposite the rigid support. A process block 106, the method 100 can include patterning a gate electrode including an active portion and an extended gate portion on the first barrier layer on a surface opposite the flexible substrate. At process block 108, the method 100 can include depositing a gate dielectric layer on the gate electrode layer and the first barrier layer on a surface opposite the flexible substrate At process block 110, the method 100 can include depositing an active channel layer on a portion of the gate dielectric layer on a surface opposite the flexible substrate, the active channel layer positioned above the active portion of the gate electrode and not above the extended gate portion of the gate electrode At process block 112, the method 100 can include depositing a first passivation layer on the active channel layer on a surface opposite the flexible substrate At process block 114, the method 100 can include forming a first opening in the gate dielectric layer and the first passivation layer to the extended gate portion of the gate electrode and forming a second and third opening in the first passivation layer to the active channel layer At process block 116, the method 100 can include patterning a first extended gate metal contact in the first opening to the extended gate portion of the gate electrode, a source metal contact in a second opening to the active channel layer, and a drain metal contact in the third opening to the active channel layer At process block 118, the method 100 can include depositing an inter-level dielectric layer on the extended gate, source, and drain metal contacts and the first passivation layer on a surface opposite the flexible substrate At process block 120, the method 100 can include opening a via in the inter-level dielectric layer to the first extended gate metal contact At process block 122, the method 100 can include depositing a second extended gate metal contact on a first portion of the inter-level dielectric layer and in the via to the first extended gate metal contact on a surface opposite the flexible substrate At process block 124, the method 100 can include depositing a surface sensing layer covering the second extended metal gate contact and on a second portion of the inter-level dielectric layer on a surface opposite the flexible substrate At process block 126, the method 100 can include depositing a surface passivation layer on the inter-level dielectric layer and a non-sensing portion of the surface sensing layer, leaving a sensing portion of the surface sensing layer exposed At process block 128, the method can include removing the flexible substrate from the rigid support.

Depositing a first barrier layer can be achieved by methods known to those having ordinary skill in the art. In certain aspects, depositing a first barrier layer can include capping the flexible substrate with a deposited nitride barrier.

Forming or patterning a gate electrode layer can be achieved by methods known to those having ordinary skill in the art. In certain aspects, forming a gate electrode layer may comprise forming a gate electrode layer disposed adjacent to a first barrier layer or a flexible substrate. In certain aspects, forming a gate electrode layer may comprise forming a molybdenum layer.

Forming an oxide gate dielectric layer or depositing a gate dielectric layer can be achieved by methods known to those having ordinary skill in the art. In certain aspects, forming an oxide gate dielectric layer may comprise forming an oxide gate dielectric layer disposed adjacent to a gate electrode layer.

Forming or depositing an active channel layer can be achieved by methods known to those having ordinary skill in the art. In certain aspects, forming an active channel layer may comprise forming an active channel layer disposed adjacent to an oxide gate dielectric layer. In certain aspects, the active channel layer is an IGZO active channel layer.

Forming a protective passivation layer or depositing a first passivation layer can be achieved by methods known to those having ordinary skill in the art. In certain aspects, forming a protective passivation layer may comprise forming a protective oxide passivation layer.

Opening contacts to the active channel layer, forming a first opening in the gate dielectric layer and the first passivation layer to the extended gate portion of the gate electrode, or forming a second and third opening in the first passivation layer to the active channel layer can be achieved by methods known to those having ordinary skill in the art, including but not limited to, etching and similar processes.

Forming a source/drain metal layer, patterning a first extended gate metal contact in the first opening to the extended gate portion of the gate electrode, patterning a source metal contact in the second opening to the active channel layer, or patterning a drain metal contact in the third opening to the active channel layer can be achieved by methods known to those having ordinary skill in the art. In certain aspects, forming a source/drain metal layer may comprise sputtering molybdenum, aluminum, or a combination thereof.

Forming or depositing an inter-level dielectric layer can be achieved by methods known to those having ordinary skill in the art. In certain aspects, forming an inter-level dielectric layer may comprise forming an inter-level dielectric layer disposed adjacent to the source/drain metal layer. In certain aspects, forming an inter-level dielectric layer may comprise spray coating a planarizing fluoropolymer.

Opening vias to the source/drain metal layer or to the first extended gate metal contact can be achieved by methods known to those having ordinary skill in the art.

Forming a metal extended gate layer or a second extended gate metal contact can be achieved by methods known to those having ordinary skill in the art. In certain aspects, forming a metal extended gate layer may comprise forming an extended metal gate layer disposed adjacent to the inter-level dielectric layer, disposed within the vias, or a combination thereof.

Forming an extended gate sensing layer or a surface sensing layer can be achieved by methods known to those having ordinary skill in the art. In certain aspects, forming an extended gate sensing layer may comprise forming an extended gate sensing layer disposed adjacent to the metal extended gate layer. In certain aspects, forming an extended gate sensing layer may comprise depositing, patterning, or depositing and patterning sequentially an indium tin oxide (ITO) layer.

Depositing a surface passivation layer can be achieved by methods known to those having ordinary skill in the art.

This disclosure provides a shatter resistant and flexible ISFET biosensor that can be built using thin-film transistor (TFT) flexible electronics display technology, for example, technology similar to the technology targeted for large area flexible electronic displays in e-books, smart phones, and tablet computers [18]. To this end, these TFTs can be very-low cost and large area. The post fabrication steps required to package and insulate these devices may be easier and more robust compared to the one for ISFETs designed on a silicon wafer substrate. Integrating these sensors with microfluidics affords a system for drug delivery [19] [20] [21], autonomous incubation of cell culture [22] [23], and application where precise control over pH is required [24]. Such devices on a flexible substrate could also be used also be used for diagnosis and health monitoring [25] [26].

Figure 3:
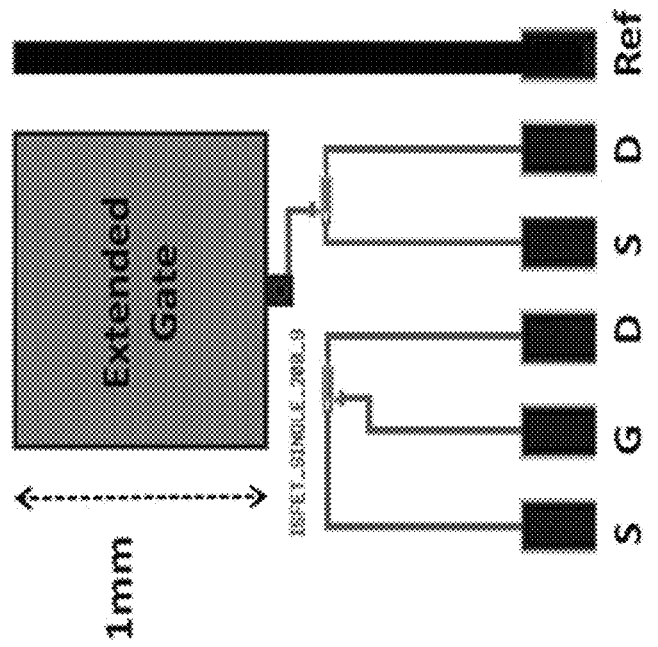
FIG. 3 is a design layout for a flexible extended gate ISFET according to one aspect of the present disclosure with a 1 mm×1 mm sensor area and a W/L=200 μm/9 μm TFT.
Figure 2:
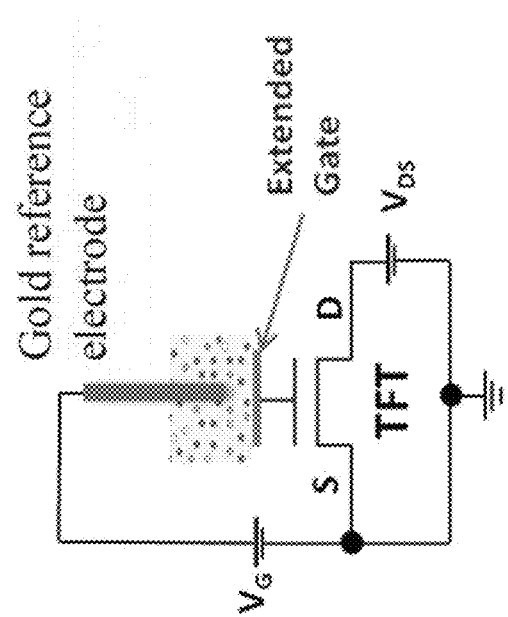
FIG. 2 is a schematic diagram of an extended gate ISFET according to one aspect of the present disclosure.

Several flexible ISFET test structures were designed and then fabricated using a baseline Indium-Gallium-Zinc Oxide (IGZO) flexible display TFT process shown in the FIG. 1. However, in the baseline flexible display process, the gate electrode layer for the TFT devices is buried and electrically isolated underneath thick insulating dielectric layers. To function as a biosensor, the pH sensitive layer needed to be brought up to the surface of the TFT device structure where it can make direct contact with an electrolyte solution. Additionally, to maximize sensitivity by increasing the physical size of the sensor, the area of the pH-sensitive layer may need to be quite large in proportion to the dimensions of the ISFET TFT transistor, which is the physical device width (W) and channel length (L) of the TFT. To address these issues, an extended gate biosensor was designed and fabricated for this work. The extended gate is constructed of a large metal gate electrode brought up to the top surface of the device [27]. This top sensor electrode (the extended gate) is then electrically connected to the gate terminal of the sub-surface conventional TFT (FIG. 2). This allows the top surface of the pH-sensitized extended metal gate to be directly exposed to the electrolyte solution. Using this approach, the size of the extended-gate top sensor electrode can be much larger than the ISFET TFT transistor devices width and length. For this work, the flexible ISFETs were designed with an extended gate sensor area of 1 mm×1 mm, connected to the gate electrode of a W/L=200 µm/9 µm TFT (FIG. 3). This provides an extended gate sensor surface that is 550 times larger than the area of the TFT gate electrode.

The flexible ISFET biosensor process uses the same thin-film transistor (TFT) process currently used to manufacture flexible electrophoretic and organic light emitting diode (OLED) displays [28]. To make the display substrate flexible, the existing fragile and rigid glass substrate used in conventional TFT display processing may be replaced with a thin and durable Dupont Teonexr PolyEthylene Naphthalate (PEN) plastic substrate. Fabrication begins with the lamination of the PEN plastic substrate to a rigid alumina carrier via a temporary adhesive [29]. To avoid exceeding the PEN substrate glass transition temperature (i.e., melt the plastic), the maximum TFT processing temperature may be limited to 200° C. The PEN plastic substrate may be capped with a deposited nitride barrier that acts as an etch stop and as a moisture barrier, which is important for biosensing applications. The TFTs for the ISFET biosensor may employ a bottom gate, inverted, or staggered device structure (FIG. 1).

For the IGZO TFT process sequence, molybdenum was first patterned to form the gate electrode metal layer, followed by a thin film deposition sequence that included an oxide gate dielectric layer, the IGZO active channel layer, and then a protective oxide passivation layer [30]. Contacts were then opened to the active layer and a direct source/drain metal connection was made using sputtered molybdenum/aluminum. Next, a planarizing fluoropolymer inter-level dielectric (ILD) layer was spray coated on the surface as an ILD layer, after which vias were opened to the source/drain metal layer. Finally, a second layer of molybdenum, followed by an indium tin oxide (ITO) layer, were deposited and patterned sequentially. In the new approach, this top layer of ITO, currently used as the transparent top electrode in the flexible OLED display process, has been repurposed to function as the extended gate pH-sensitive layer. While not commonly used as an ISFET sensor layer, ITO has previously been shown to provide a linear response to pH for ISFETs on glass substrates between pH2 and pH12 [31]. This enables use of existing flexible display TFT process sequence, and has the added advantage of demonstrating a pH sensor layer (ITO) common to most commercial organic light emitting diode (OLED) and liquid crystal display (LCD) TFT-based display processes.

At this point, the flexible ISFET test structures were debonded from the temporary alumina carrier simply by peeling off the entire PEN plastic substrate. Scissors were then used to singulate and trim the individual flexible ISFET test structures to size. To form the integrated flexible reference electrode, a gold-plated printed circuit board (PCB) trace trimmed from a separate flexible substrate was positioned immediately adjacent to the 1×1 mm extended gate. Alternative aspects, described below in Section 6, used a printed flexible Silver/Silver-Chloride (Ag/AgCl) ink for the reference electrode [17]. However, it was found that after electrolyte immersion for several days, the chlorine from the printed Ag/AgCl reference electrode begins to etch the ITO sensor layer on the extended gate electrode. Switching to gold for the reference electrode eliminated this issue. In a production version, the separate gold-plated reference electrode would be replaced by gold trace, patterned directly on the flexible plastic substrate. To make the external electrical connections, heat-seal flex was then bonded to the drain (D) and source (S) bond pads on the TFT test structure, along with the gold reference electrode, followed by bonding to a small separate breakout PCB. Low cost GBC heat seal thermal lamination film was then applied to provide both electrical isolation and environmental encapsulation for the flexible ISFET test structures. To encapsulate (laminate), a small hole that exposed both a portion of the gold reference electrode and the entire 1 mm² ITO sensor electrode was punched in the top sheet of the thermal lamination film, and the bottom sheet of lamination film was positioned under the ISFET test structure. A thin temporary sheet of Teflon was then placed over the top of the assembly to protect the sensor electrode and the entire flexible assembly was run through 110° C. rollers to activate the adhesive and seal the assembly.

ISFET is a field effect transistor with a gate in the form of a reference electrode dipped in the solution. The pH sensitivity of an ISFET arises from the interaction of ions with the insulator gate surface sites which changes the surface potential at the gate insulator and electrolyte interface. Thus the insulator defines the sensitivity of the pH sensor. Theoretically, the sensitivity to H+ ions of the sensor is given by the Nernst equation shown in [32]. Change in pH manifests as change in surface potential, potential at the insulator-electrolyte interface, which in turn changes the threshold voltage of the device as shown in the FIG. 4.

Figure 4:
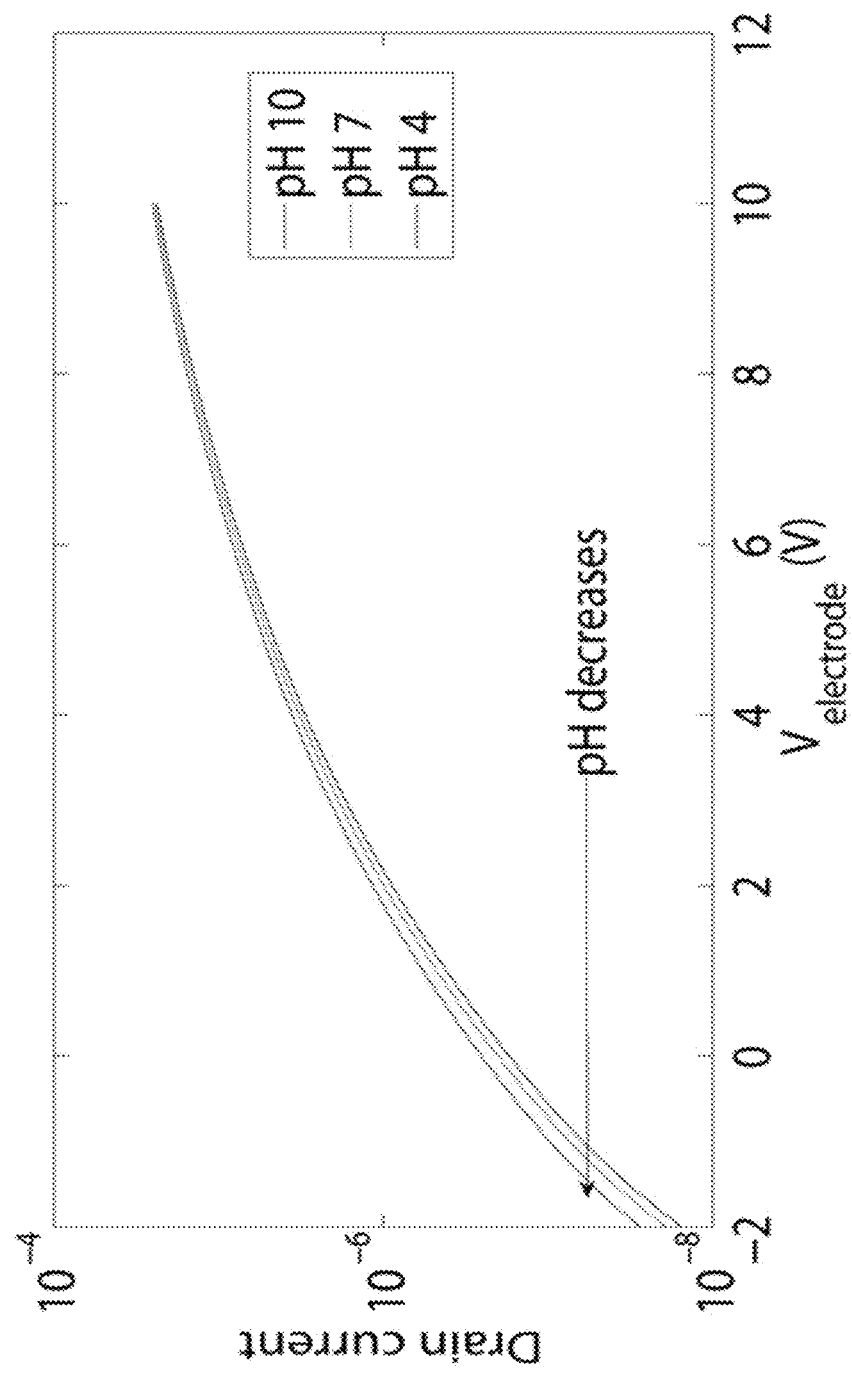
FIG. 4 is a graph of the drain current versus electrode potential for an ISFET according to one aspect of the present disclosure for different pH buffer solutions. The drain to source potential was kept at 5 volts.
Figure 5:
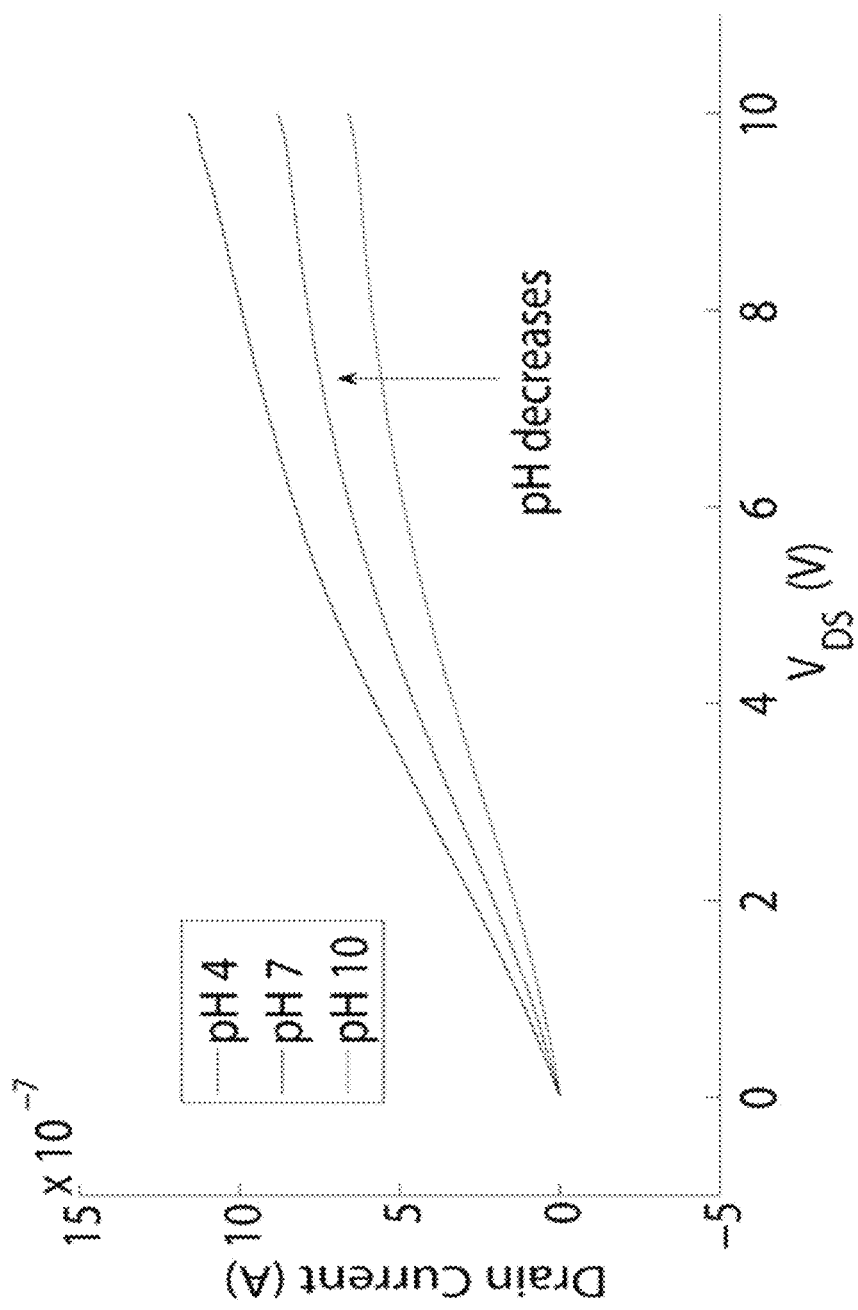
FIG. 5 shows the drain current of an ISFET according to one aspect of the present disclosure versus drain voltage for electrolytes having different pH values.

The transfer characteristics of the ISFET, fabricated as discussed in above, is shown in the FIGS. 4 and 5. FIG. 4 shows the response of the ISFET while varying the potential of the reference electrode keeping the drain to source potential. The FIG. 5 shows the channel current of the ISFET while varying the drain to source potential of the ISFET. The ISFET showed a sensitivity of 50 mV/pH as observed in the FIG. 4. As observed the sensitivity of ITO layer to pH is lesser than the ideal nernstian response but is adequate for the application described in the Section 1.

Figure 6:
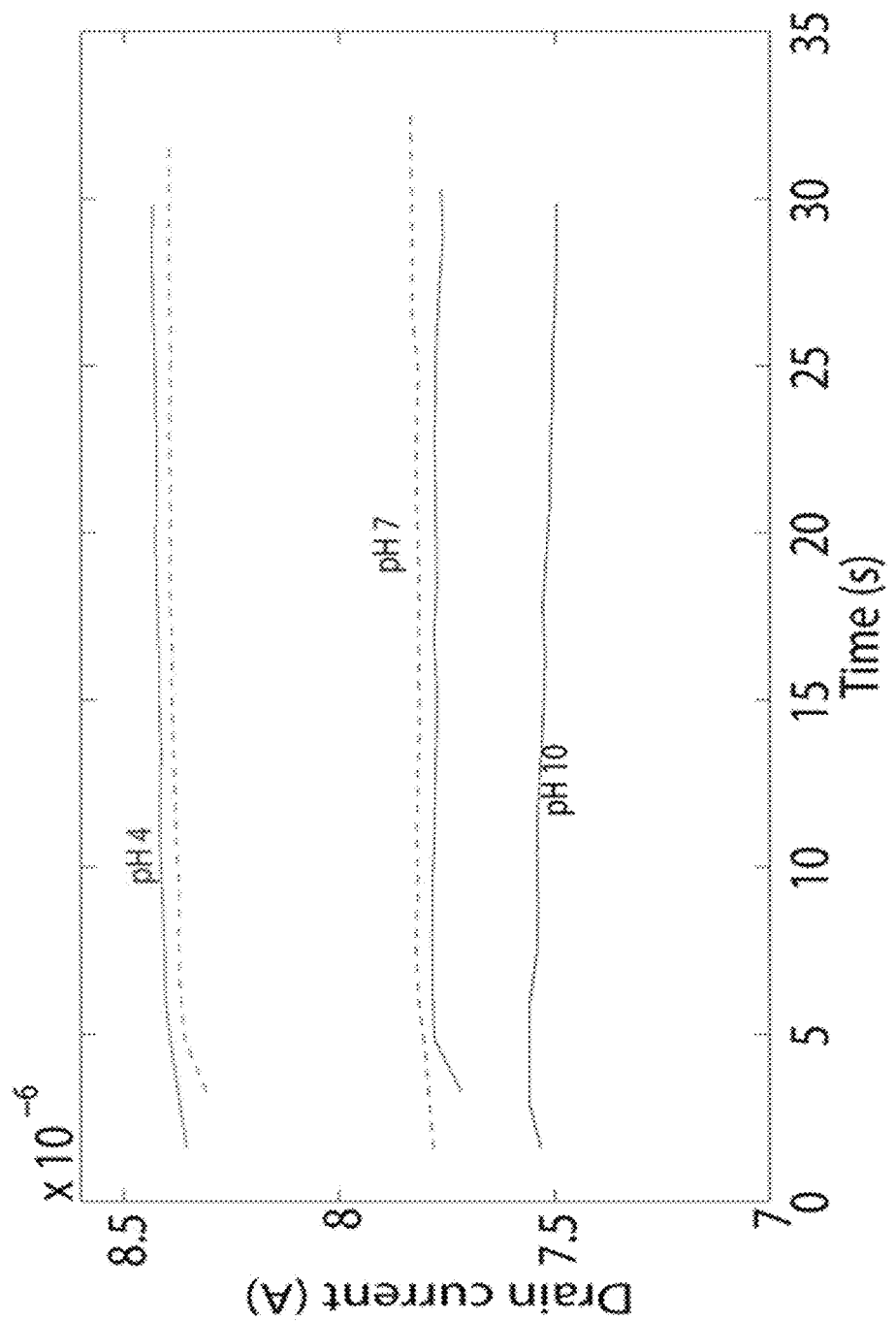
FIG. 6 is a graph showing the response of an ISFET according to one aspect of the present disclosure to different pH solutions. The dashed line corresponds to a second reading. A drift in threshold voltage can be seen.
Figure 7:
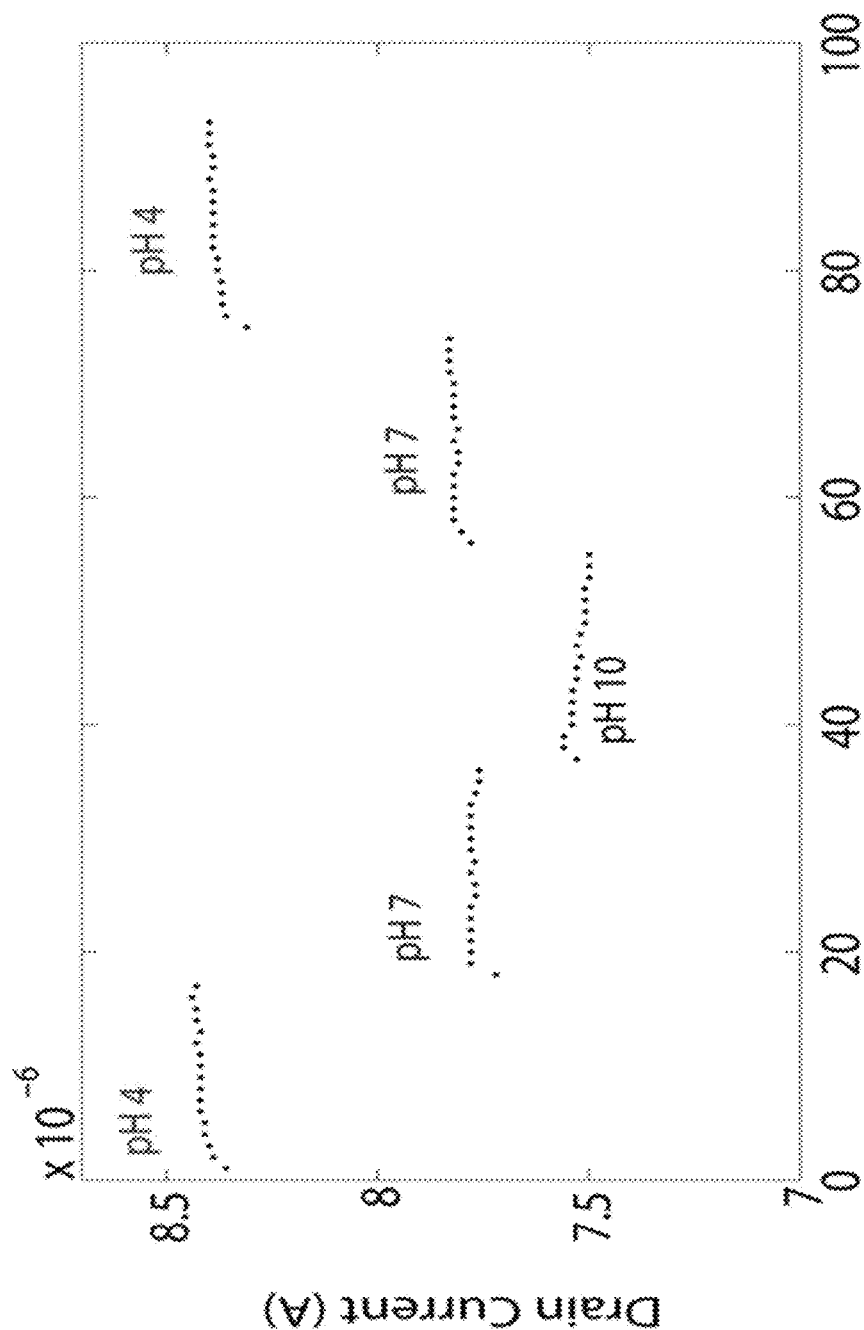
FIG. 7 is the graph of FIG. 6 plotted continuously to show the repeatability of the devices.

Repeatability of an ISFET is usually evaluated by alternating the pH of the solution and measuring its output [33]. Hence to see the repeatability of the device its response was measured for varying pH values. As seen in the FIGS. 6 and 7 the output current was measured while varying the pH in the following manner 4, 7, 10, 7, and 4. In between each measurement the surface of the sensors was treated with DI water and ethanol to remove the residue. Each time the pH was measured with a solution having a volume of 10 µl, and the variation in the current, seen in the FIGS. 6 and 7, could be due to the position of the droplet with respect to the sensing area and the gold reference electrode. These experiments were performed without a sample well, and stability could be increased by employing a sample well.

Three different devices were fabricated and designed on the flexible ISFET. An ISFET designed on a flexible substrate suffers from mismatch not only due to process variation [34] but also due variation in packaging of these devices. Mismatch in the sensor output could lead to potential errors in the measurement of the pH. Three different ISFET designed on a flexible substrate were measured to characterize the variation in these devices. Variation in the output of the pH sensor could be easily calibrated by using signal processing circuits, because the sensitivity of these devices are similar. Calibrating would require measuring this signal and processing the output on a CMOS chip. Hence towards this goal a readout circuit was designed in a 0.5 µm CMOS process.

Figure 8:
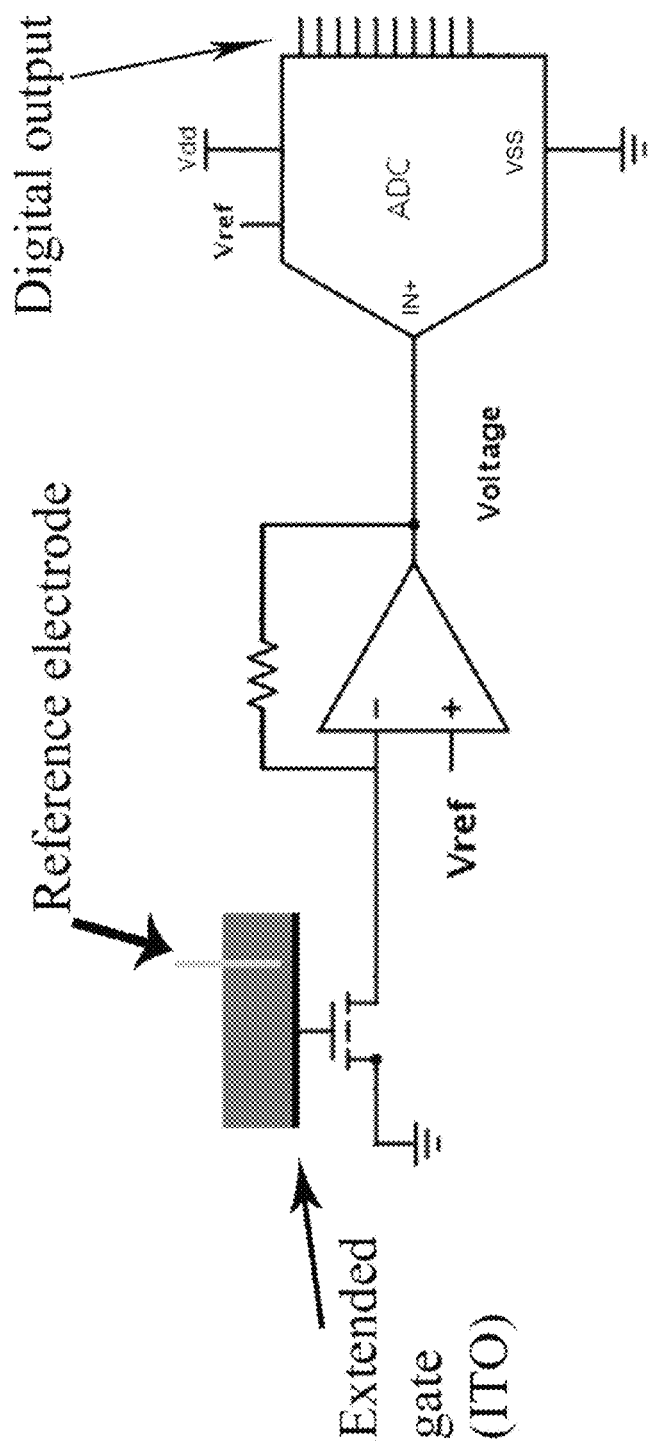
FIG. 8 is a block diagram of a readout circuit employed to measure the output of the flexible ISFET. An extended gate flexible ISFET with a gold reference electrode is used for measuring the pH. A transimpedance amplifier is used for the converting current to voltage. The digitization of this signal could be done using a 10 bit dual slope ADC.

In general a readout circuit is used to convert analog output of a sensors into a digital bits for signal processing. Since flex does not allow signal processing to be done efficiently it is optimal to leverage the CMOS technology for it. Thus a readout circuit was designed in a 0.5 µm CMOS process. A readout circuit employs a current to voltage converter, usually a transimpedance amplifier, and an Analog to Digital Converter (ADC), a 10 bit dual slope ADC in an exemplary case. A basic block diagram of the readout circuit is shown in the FIG. 8.

A TransImpedance Amplifier (TIA) uses a feedback resistor to convert current to voltage. The TIA uses a folded cascode amplifier, having a specification shown in the Table 1, designed in a 0.5 µm process. Folded cascade amplifier allows us to have a higher voltage swing and higher gain. An external feedback resistor was used since the response of the flexible ISFET was not known a priori. The sensitivity of the output is dependant on the value of the feedback resistor and so is the input referred current and voltage noise. The output of the TIA for varying pH values is shown in the FIG. 9.

TABLE 1

| Specification | Value |
| --- | --- |
| Gain | 61.85 dB |
| −3 dB cut-off frequency | 10.26 kHz |
| Funity | 13.1 MHz |
| Phase margin | 80° |
| PSRR | 64 dB |
| CMRR | 95 dB |
| Slew Rate | 6 V/µs |
| Power (5 volts) | 1.8 mW |
| Area | 210 µm * 209 µm |

Figure 9:
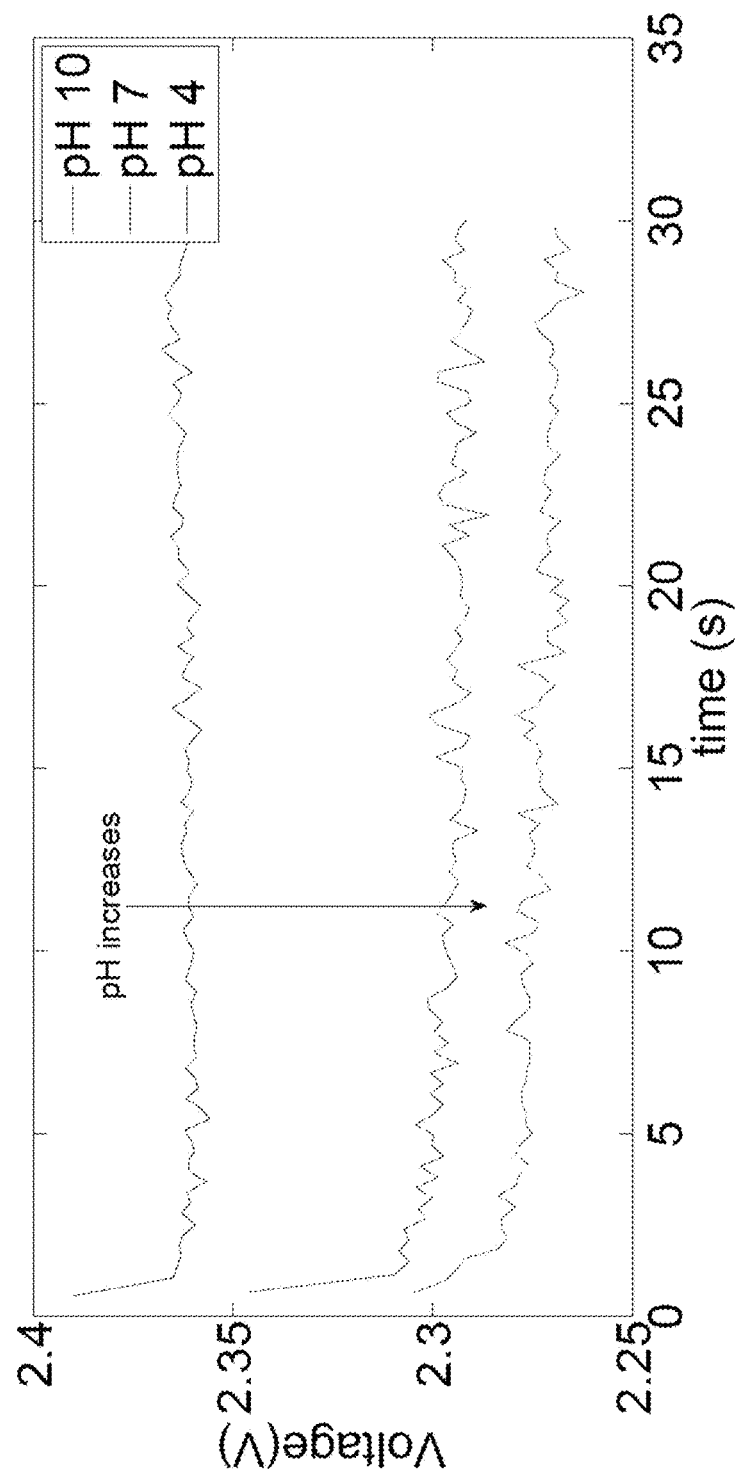
FIG. 9 is a plot of the output of the readout circuit shown in FIG. 8 measured with buffers having varying pH.

To take advantage of the digital signal processing capabilities of a computer the analog signal shown in the FIG. 9 has to be converted into digital bits. Thus a 10-bit chopper stabilized dual slope ADC, which gives a very high resolution for low frequency application, is designed in a CMOS process to digitize the output of the biosensor.

For biological applications pH is a slow varying process with a frequency in few Hz or mHz. At such low frequencies flicker noise, caused due to random trapping and detrapping of charges in the oxide of semiconductor device [35], is dominant and determines the smallest signal which could be detected. Thus the above OTA, having the specification given in the table 1, was modified to a chopper stabilized OTA to be used as a part of the integrator in the ADC.

Chopper stabilization is used to reduce input referred offset and noise [36], for a continuous system. Chopper stabilization can reduce the flicker noise by ten times.

The above described chopper stabilized folded cascode is used as a part of the integrator in the 10 bit dual slope ADC. It should be appreciated that many different ADCs could be deployed with this disclosure and that systems described herein could interface with a computer.

Figure 11:
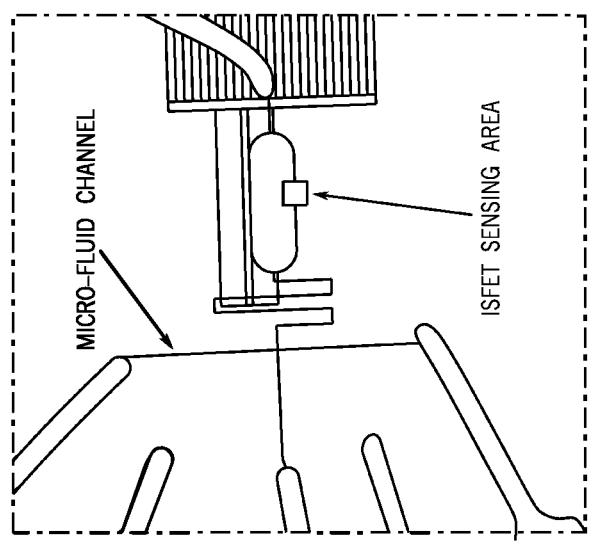
FIG. 11 is an image a flexible ISFET coupled to a microfluidic channel.
Figure 10:
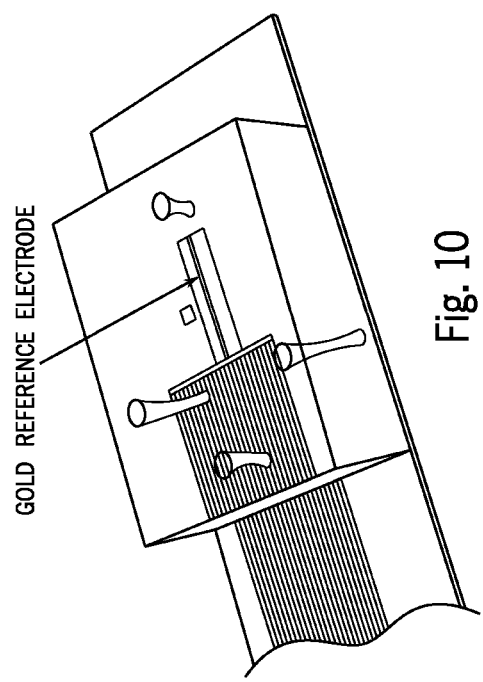
FIG. 10 shows an image of a cross section of polydimethylsiloxane (PDMS) integrated with a flexible ISFET according to one aspect of the present disclosure.

This disclosure provides a low cost biosensing system by taking advantage of the large sensing area provided by the flexible TFT process and the signal processing capabilities of CMOS. The ease of post processing steps allows seamless integration of these devices with microfluidics as shown in the FIGS. 10 and 11. Also insulating electrical parts from the electrolyte can be done with relative ease using a flexible substrate compared to pH sensors designed on CMOS, where flip chip [37] or extra post processing steps are required for insulating the wire bonds. Certain applications, such as cell culture [24] or for stability of proteins [38], requires precise control over pH and hence future work would be towards developing such a biosensing platform.

The work demonstrates the use of indium tin oxide, which is commonly used as anode for OLED, as a pH sensitive material. A sensitivity of 50 mV/pH was observed which is less than theoretical nernstian response. Variability in these devices could be easily calibrated by processing the signal on CMOS and the circuit used for interfacing with CMOS is presented here. The use of flexible substrate reduces the cost of the biosensors to pennies per $cm^2$ which is important and advantageous for developing low cost and portable medical devices.

In certain aspects, the glass or silicon substrate used for conventional ISFETs has been replaced with a 125 um thick flexible Dupont Teijin Films Teonex® polyethylene naphthalate (PEN) plastic substrate. To evaluate the new concept, a prototype flexible extended gate pH biosensor was assembled using a TFT parametric test structure trimmed from a 370×470 mm Gen2 plastic substrate which was originally used for a large-area, flexible, OLED display demonstration. [18] A 1 mm wide gate (G) bond pad for the W/L=9/9 μm indium gallium zinc oxide (IGZO) TFT test structure is left unconnected, and functions as the extended gate for the new flexible ISFET. The top metal layer of indium tin oxide (ITO), used as the transparent top electrode in the flexible OLED display process, has been repurposed to function as the extended gate pH-sensitive layer in the prototype flexible ISFET. This avoided the need to make any changes to existing Gen2 flexible OLED display TFT process sequence, and has the added advantage of demonstrating a pH sensor layer (ITO) common to most commercial OLED and LCD display processes. To complete the assembly, heat-seal flex was bonded to the drain (D) and source (S) bond pads on the TFT test structure and then bonded to a small breakout PCB. To form the integrated flexible reference electrode, a small dot of silver epoxy was first deposited, and then a 30 ga wire bonded to the dot was run to the PCB. Next an ~700 μm wide reference electrode was printed using flexible Silver/Silver-Chloride (Ag/AgCl) ink (Creative Materials 124-36) on the nitride passivation layer and connected to the silver epoxy dot in the space between the gate and drain bond pads. In a production version, the wire lead would be replaced by a metal trace. Finally, an ~3 mm long shallow well for the pH solution was formed over both the extended ITO gate and Ag/AgCl reference electrode using a thin layer of solvent-free epoxy. This created an active (ITO) sensor area of approximately 1×3 mm. The drain, source, and reference electrode leads on the PCB were then connected to a Keithley SourceMeter to measure the current-voltage device characteristics, with the gate bias on the reference electrode set to +10 volts, and the drain-to-source bias set to +5 volts.

The well was then filled with different pH buffer concentrations using the sequence of pH 4→pH 7→pH 10→pH 7→pH 4, with a sample interval of 400 seconds for each pH concentration, and with the ISFET drain current sampled from 0 to 10, 200 to 210, and 400 to 410 seconds in each interval. In typical operation, it is assumed that the ISFET will also be similarly sampled and then turned off to reduce dynamic power consumption. A decrease in the flexible ISFET drain current was correctly observed as the pH concentration increased from pH 4 to pH 10, confirming decreasing H+ ion protonation of the ITO extended-gate electrode surface as the pH concentration was increased. ISFET stability and discrimination were also shown to improve at longer measurement intervals, with an observed average 4.7% difference in measured ISFET drain current between the three different pH buffer concentrations at 400 seconds. The most significant downward drift in ISFET drain current occurred during consecutive measurements in the initial 0 to 10 second sample period, which is attributed to hydration of the ITO pH sensor layer surface. [16] The pH response was also demonstrated to be repeatable over multiple pH cycles with the average ISFET drain current in the second pH 4 cycle identical to the initial measurement at 400 seconds.

REFERENCES

[1] P. Bergveld, Development of an ion-sensitive solid-state device for neurophysiological measurements, Biomedical Engineering, IEEE Transactions on BME-17 (1970) 70-71.

[2] C. Jimenez-Jorquera, J. Orozco, A. Baldi, Isfet based microsensors for environmental monitoring, Sensors 10 (2009) 61-83.

[3] E. Sharon, R. Freeman, I. Willner, Detection of explosives using field-effect transistors, Electroanalysis 21 (2009) 2185-2189.

[4] C.-S. Lee, S. K. Kim, M. Kim, Ion-sensitive field-effect transistor for biological sensing, Sensors 9 (2009) 7111-7131.

[5] P. Bergveld, Thirty years of ISFETOLOGY: What happened in the past 30 years and what may happen in the next 30 years, Sensors and Actuators B: Chemical 88 (2003) 1-20.

[6] M. L. Metzker, Sequencing technologies the next generation, Nature Reviews Genetics 11 (2010) 31-46.

[7] D.-S. Kim, Y.-T. Jeong, H.-J. Park, J.-K. Shin, P. Choi, J.-H. Lee, G. Lim, An fet-type charge sensor for highly sensitive detection of {DNA} sequence, Biosensors and Bioelectronics 20 (2004) 69-74. Microsensors and Microsystems 2003.

[8] C. Toumazou, L. M. Shepherd, S. C. Reed, G. I. Chen, A. Patel, D. M. Garner, C.-J. A. Wang, C.-P. Ou, K. Amin-Desai, P. Athanasiou, H. Bai, I. M. Q. Brizido, B. Caldwell, D. Coomber-Alford, P. Georgiou, K. S. Jordan, J. C. Joyce, M. La Mura, D. Morley, S. Sathyavruthan, S. Temelso, R. E. Thomas, L. Zhang, Simultaneous DNA amplification and detection using a pH-sensing semiconductor system, NATURE METHODS 10 (2013) 641+.

Jonathan M. Rothberg, Wolfgang Hinz, Todd M. Rearick, Jonathan Schultz, William Mileski, Mel Davey, John H.

Leamon, Kim Johnson et. al., An integrated semiconductor device enabling non-optical genome sequencing, Nature 475 (2011) 348352.

[10] Z. Selvanayagam, P. Neuzil, P. Gopalakrishnakone, U. Sridhar, M. Singh, L. Ho, An isfet-based immunosensor for the detection of beta-bungarotoxin, Biosensors and Bioelectronics 17 (2002) 821-826.

[11] M. J. Schoning, A. Poghossian, Recent advances in biologically sensitive field-effect transistors (biofets), Analyst 127 (2002) 1137-1151.

[12] S. Meyburg, M. Goryll, J. Moers, S. Ingebrandt, S. Bcker-Meffert, H. Lth, A. Offenhusser, N-channel field-effect transistors with floating gates for extracellular recordings, Biosensors and Bioelectronics 21 (2006) 1037-1044.

[13] D. Welch, S. Shah, S. Ozev, J. Blain Christen, Experimental and simulated cycling of ISFET electric fields for drift reset, Electron Device Letters, IEEE 34 (2013) 456-458.

[14] H. van den Vlekkert, U. Verkerk, P. van der Wal, A. van Wingerden, D. Reinhoudt, J. Haak, G. Honig, H. Holterman, Multi-ion sensing device for horticultural application based upon chemical modification and special packaging of {ISFETs}, Sensors and Actuators B: Chemical 6 (1992) 34-37.

[15] P. Estrela, S. D. Keighley, P. Li, P. Migliorato, Application of thin film transistors to label-free electrical biosensors, in: Industrial Electronics, 2008. ISIE 2008. IEEE International Symposium on, pp. 2034-2039.

[16] J. Pinto, R. Branquinho, P. Barquinha, E. Alves, R. Martins, E. Fortunato, Extended-gate isfets based on sputtered amorphous oxides, Display Technology, Journal of 9 (2013) 729-734.

[17] J. Smith, S. Shah, M. Goryll, J. Stowell, D. Allee, Flexible isfet biosensor using igzo metal oxide tfts and an ito sensing layer, Sensors Journal, IEEE PP (2013) 1-1.

[18] B. O'Brien, Y. K. Lee, M. Marrs, J. Smith, M. Strnad, E. Forsythe, D. Morton, 14.7" active matrix pholed displays on temporary bonded pen substrates with low temperature igzo tfts, SID Symposium Digest of Technical Papers 44 (2013) 447-450.

[19] I. U. Khan, C. A. Serra, N. Anton, T. Vandamme, Microfluidics: A focus on improved cancer targeted drug delivery systems, Journal of Controlled Release 172 (2013) 1065-1074.

[20] F. S. Majedi, M. M. Hasani-Sadrabadi, S. Hojjati Emami, M. A. Shokrgozar, J. J. VanDersarl, E. Dashtimoghadam, A. Bertsch, P. Renaud, Microfluidic assisted self-assembly of chitosan based nanoparticles as drug delivery agents, Lab Chip 13 (2013) 204-207.

[21] W. R. D. Douglas B. Weibel, G. M. Whitesides, Microfabrication meets microbiology, Nature Reviews Microbiology 5 (2007) 209-218.

[22] J. Blain Christen, A. Andreou, Integrated pdms/cmos microsystem for autonomous incubation and imaging in cell culture studies, in: Life Science Systems and Applications Workshop, 2006. IEEE/NLM, pp. 1-2.

[23] J. Christen, A. Andreou, Design, fabrication, and testing of a hybrid cmos/pdms microsystem for cell culture and incubation, Biomedical Circuits and Systems, IEEE Transactions on 1 (2007) 3-18.

[24] D. Welch, J. B. Christen, Real-time feedback control of ph within microfluidics using integrated sensing and actuation, Lab Chip 14 (2014) 1191-1197.

[25] Donghee Son, Jongha Lee, Shutao Qiao et. al., Multifunctional wearable devices for diagnosis and therapy of movement disorders, NATURE NANOTECHNOLOGY (9 Oct. 2013).

[26] J. A. Rogers, Y. Huang, A curvy, stretchy future for electronics, Proceedings of the National Academy of Sciences 106 (2009) 10875-10876.

[27] P. Georgiou, C. Toumazou, {ISFET} characteristics in {CMOS} and their application to weak inversion operation, Sensors and Actuators B: Chemical 143 (2009) 211-217.

[28] G. B. Raupp, S. M. O'Rourke, C. Moyer, B. P. O'Brien, S. K. Ageno, D. E. Loy, E. J. Bawolek, D. R. Allee, S. M. Venugopal, J. Kaminski, D. Bottesch, J. Dailey, K. Long, M. Marrs, N. R. Munizza, H. Haverinen, N. Colaneri, Low-temperature amorphous-silicon backplane technology development for flexible displays in a manufacturing pilot-line environment, Journal of the Society for Information Display 15 (2007) 445-454.

[29] J. Haq, S. Ageno, G. B. Raupp, B. D. Vogt, D. Loy, Temporary bond-debond process for manufacture of flexible electronics: Impact of adhesive and carrier properties on performance, Journal of Applied Physics 108 (2010)-.

[30] M. Marrs, C. Moyer, E. Bawolek, R. Cordova, J. Trujillo, G. Raupp, B. Vogt, Control of threshold voltage and saturation mobility using dual-active-layer device based on amorphous mixed metaloxidesemiconductor on flexible plastic substrates, Electron Devices, IEEE Transactions on 58 (2011) 3428-3434.

[31] J.-L. Chiang, S.-S. Jhan, S.-C. Hsieh, A.-L. Huang, Hydrogen ion sensors based on indium tin oxide thin film using radio frequency sputtering system, Thin Solid Films 517 (2009) 4805-4809. 4th International Conference on Technological Advances of Thin Films and Surface Coatings.

[32] F. Winquist, Biosensors—an introduction, Measurement Science and Technology 9 (1998).

[33] T. Ito, H. Inagaki, I. Igarashi, Isfet's with ion-sensitive membranes fabricated by ion implantation, Electron Devices, IEEE Transactions on 35 (1988) 56-64.

[34] M. Pelgrom, A. C. J. Duinmaijer, A. Welbers, Matching properties of mos transistors, Solid-State Circuits, IEEE Journal of 24 (1989) 1433-1439.

[35] F. Hooge, 1/f noise sources, Electron Devices, IEEE Transactions on 41 (1994) 1926-1935.

[36] C. Enz, G. Temes, Circuit techniques for reducing the effects of op-amp imperfections: autozeroing, correlated double sampling, and chopper stabilization, Proceedings of the IEEE 84 (1996) 1584-1614.

[37] D. Welch, J. Blain Christen, Seamless integration of CMOS and microfluidics using flip chip bonding, Journal of Micromechanics and Microengineering 23 (2013).

[38] J. Warwicker, Simplified methods for pka and acid ph-dependent stability estimation in proteins: Removing dielectric and counterion boundaries, Protein Science 8 (1999) 418-425.

The invention claimed is:

1. A flexible ion-selective field effect transistor comprising:
 a flexible substrate;
 a thin film transistor disposed on the flexible substrate, the thin film transistor including a source, a drain, a gate, and an active channel layer, the gate is isolated from the atmosphere; and
 a surface sensing layer in electronic communication with the gate, wherein the flexible ion-selective field effect transistor has a structure that provides a flexible thin film transistor display, wherein the flexible thin film transistor display is provided when the surface sensing layer is only in electronic communication with the source or the drain, wherein the surface sensing layer serves as a transparent top electrode of the flexible thin film transistor display.

2. The flexible ion-selective field effect transistor of claim 1, wherein the active channel layer is indium gallium zinc oxide or amorphous silicon.

3. The flexible ion-selective field effect transistor of claim 1, wherein the surface sensing layer is indium tin oxide.

4. The flexible ion-selective field effect transistor of claim 1, further comprising a reference electrode.

5. The flexible ion-selective field effect transistor of claim 1, further comprising a sample well positioned around at least part of the surface sensing layer and configured to retain a liquid in contact with the surface sensing layer.

6. The flexible ion-selective field effect transistor of claim 1, wherein the thin-film transistor has a configuration selected from the group consisting of bottom gate, inverted, staggered, and combinations thereof.

7. A sensor array comprising a plurality of the flexible ion-selective field-effect transistor of claim 1.

8. The sensor array of claim 7, wherein two of the plurality of flexible ion-selective field effect transistors are sensitive to different analytes.

9. A microfluidic device comprising:
a microfluidic channel in fluid communication with a microfluidic reservoir; and
the flexible ion-selective field effect transistor of claim 1, wherein a fluid in the microfluidic reservoir contacts at least part of the surface sensing layer.

10. The microfluidic device of claim 9, wherein the flexible ion-selective field effect transistor includes a reference electrode and the fluid in the microfluidic reservoir contacts at least part of the reference electrode.

11. A flexible pH sensor comprising:
a flexible substrate;
a thin-film transistor disposed on the flexible substrate, the thin film transistor having a source, a drain, and a gate; and
a surface sensing layer comprising a material suitable for use as a transparent top electrode in a flexible organic light emitting diode, the surface sensing layer in physical contact with the gate,
wherein the flexible pH sensor has a structure that provides a flexible thin film transistor display, wherein the flexible thin film transistor display is provided when the surface sensing layer is only in electronic communication with the source or the drain, wherein the surface sensing layer serves as a transparent top electrode of the flexible thin film transistor display.

12. The flexible pH sensor of claim 11, wherein the material suitable for use as the transparent top electrode in the flexible organic light emitting diode is indium tin oxide.

* * * * *